United States Patent [19]

Winkelman

[11] Patent Number: 4,998,533
[45] Date of Patent: Mar. 12, 1991

[54] APPARATUS AND METHOD FOR IN VIVO ANALYSIS OF RED AND WHITE BLOOD CELL INDICES

[76] Inventor: James W. Winkelman, 62 Rangeley Rd., Brookline, Mass. 02167

[21] Appl. No.: 320,896

[22] Filed: Mar. 9, 1989

Related U.S. Application Data

[63] Continuation of Ser. No. 165,287, Mar. 8, 1988, abandoned, which is a continuation-in-part of Ser. No. 886,306, Jul. 15, 1986, abandoned.

[51] Int. Cl.$^5$ .......................... A61B 1/04; A61B 3/12; A61B 5/02
[52] U.S. Cl. ................................ 128/637; 128/653 R; 128/666; 128/745
[58] Field of Search ........ 128/632, 633, 637, 665–668, 128/653, 745

[56] References Cited

U.S. PATENT DOCUMENTS

| 4,194,217 | 3/1980 | van den Bosch | 128/633 |
| 4,305,398 | 12/1981 | Sawa | 128/666 |
| 4,331,132 | 5/1982 | Mukasa | 128/745 |

OTHER PUBLICATIONS

Devaney et al, ISA Trans, vol. 15, No. 1, 1976, pp. 73–78.
Fesler, Computers in Cardiology, Sep. 1979, pp. 379–382.
Brown, IEEE Trans. Biomed. Engr., vol. BME-27, No. 3, Mar. 1980, pp. 132–138.
Miller, IEEE Trans. Biomed Engr., vol. BME-23, No. 5, pp. 400–405, Sep. 1976.
Megla, SID Journal, vol. 11, No. 5, Sep.–Oct. 1974, pp. 20–22.
Johnson, *Red Cell Separation in the Mesenteric Capillary Network*, vol. 221, No. 1, American Journal of Physiology, Jul. 1971.
Fagrell, Fronek, and Intaglietta, *A Microscope-Television System For Studying Flow Velocity In Human Skin Capillaries*, American Journal of Physiology, vol. 233, No. 2, (1977).
Fagrel, Intaglietta and Ostergren, *Relative Hematocrit in Human Skin Capillaries and Its Relation to Capillary Blood Flow Velocity*, Microvascular Research, vol. 20, pp. 327–335 (1980).
Safranyos, Ellis, Tyml, and Groom, *Heterogeneity of Capillary Diameters in Skeletal Muscle of the Frog*, Microvascular Research, vol. 26, pp. 151–156 (1983).
Mickols, Maestre, Tinoco, Jr., and Embury, *Visualization of Oriented Hemoglobin S in Individual Erythrocytes by Differential Extinction of Polarized Light*, Proceedings of the National Academy of Sciences, U.S.A., vol. 82, pp. 6527–6531, Oct. 1985.
Ellis, Safranyos, and Groom, *Television-Computer Method for in Vivo Measurement of Capillary Diameter, Based on the Passage of Red Cells*, Microvascular Research, vol. 26, pp. 139–150 (1983).

Primary Examiner—William E. Kamm
Assistant Examiner—John Hanley
Attorney, Agent, or Firm—Dilworth & Barrese

[57] ABSTRACT

Apparatus and methods for in vivo determination of red and white blood cell characteristics from a flow of red and white blood cells in mucous membranes are provided wherein image capturing means are employed to optically isolate images from a flow of blood cells and transmit those images to an image receiving means for encoding into electronic signals. The images are also filtered through light filters and subsequently transmitted to a computer for evaluation and analysis. The results of this analysis are then made available for display either on a CRT or hard copy printer.

22 Claims, 2 Drawing Sheets

APPARATUS AND METHOD FOR IN VIVO ANALYSIS OF RED AND WHITE BLOOD CELL INDICES

REFERENCE TO RELATED APPLICATIONS

This is a continuation of co-pending application Ser. No. 07/165,287, filed on Mar. 8, 1988 now abandoned, which is a continuation-in-part of application Ser. No. 06/886,306 filed July 15, 1986 now abandoned.

FIELD OF THE INVENTION

The present invention relates to the measurement of blood cell indices and, more particularly, to apparatus and methods for in vivo quantitative measurement of red and white blood cell indices.

BACKGROUND OF THE INVENTION

The red blood cell count, white blood cell count and the determination of blood cell indices are the most frequent of all clinical laboratory tests performed on patients in doctors' offices, clinics and hospitals in the United States and throughout the world. These tests provide essential information as to the health characteristics of individuals of all age groups.

Processes for evaluating and testing blood which are in widespread use in the art today uniformly require a sample of blood to be removed from the body for testing and analysis. The procedure for taking blood, known as phlebotomy, ordinarily involves the removal of blood from capillary or peripherial blood (usually in infants) and venous blood. Only certain licensed persons are permitted by law to carry out this procedure. These include nurses, laboratory technicians, physicians, and other specially trained persons.

In infant phlebotomies, the sample is ordinarily taken from the palmar surfaces of the tip of a finger or the plantar surfaces of the great toe or heel. The site is first rubbed vigorously with a gauze pad moistened with seventy-percent alcohol to remove dirt and debris and to increase blood circulation. Once the skin has dried, a puncture 2-3 mm deep is made with a blade or lancet. After the sample has been collected, slight pressure is applied to the area of the puncture with a gauze pad. This procedure is usually painful and frightening to the infant which results in further difficulties in effecting the phlebotomy.

The most common form of adult patient phlebotomy involves the removal of venous blood through puncture of a vein in the patient's arm. This procedure is also somewhat painful and is viewed with apprehension by most patients. Veins must be carefully inspected, particularly with those patients who have already had numerous punctures. The patient's life may depend on vein patency, and care must be taken to preserve these vessels. Hematomas or ecchymoses are usually evidence of the operator's poor technique or judgment.

The equipment necessary for this procedure ordinarily includes a syringe and a needle of the appropriate diameter. This needle must be carefully inspected as a blunt or bent tip will damage the patient's vein and often lead to failure to collect blood from the vein. A tourniquet is also used in the procedure in order to make the veins more prominent and help to eliminate blind probing.

The procedure involves making the patient comfortable, preferably having them sit in a chair with the patient's arm accessible to the operator. The tourniquet is then applied and the skin surrounding the target site is cleaned with a seventy-percent alcohol solution and permitted to dry. Once the appropriate vein has been located, the needle is pushed into the vein with a single direct puncture of both the skin and the vein. The tourniquet is then loosened and the desired amount of blood is obtained. The operator must be aware of the patient at all times as the trauma of venipuncture can cause the patient to faint. After the procedure is completed the operator must also insure that the patient's condition is satisfactory before he is dismissed.

Complications of venipunctures do occur and include a measurable increase in the concentration of blood cells when the tourniquet is applied for periods greater than sixty seconds. Failure of the blood to enter the syringe may also occur. This may result from excessive pull on the plunger of the syringe which can cause the vein to collapse. The piercing of the outer coat of the vein without entering the lumen can also account for failure. These complications are occasionally followed by hematoma formation. When this occurs, the needle must be withdrawn and the procedure must be carried out on the other arm. Late complications include possible thrombosis of the vein due to trauma, especially following many venipunctures at the same site. Finally, where non-disposable or contaminated needles are used, the transmission of contagious diseases such as serum hepatitis, etc. may be effected.

Blood removed from the patient's body is usually transported to a clinical laboratory where it is tested and the results are sent back to the requesting physician. In most doctors' offices in the Untied States today, such tests are performed at central laboratories and the results are usually available the following day. In addition to the delay, there is also a substantial cost for such testing because of the logistics involved in specimen collection, transport, laboratory accessioning, skilled and licensed personnel required for the removal procedure and testing of the specimens, reagents utilized and expensive instrumentation employed. Further disadvantages of this in vitro method include the numerous sources of error introduced into the analysis of the specimen as a result of in vitro changes in the blood sample. For example, in blood kept at room temperature, swelling of the red blood cells between six and twenty-four hours raises the hematocrit and mean corpuscular volume (MCV) and lowers the mean corpuscular hemoglobin concentration and the red blood cell sedimentation rate.

Current in vitro testing requires strict adherence to procedure. Before taking a sample from a tube of venous blood for hematologic determination, it is important that the blood be mixed thoroughly. If the tube has been standing, this requires at least sixty inversions of the tube or two minutes on a mechanical rotator; less than this leads to unacceptable deterioration in precision.

The most common tests performed on blood samples taken from patients are the hematocrit (Hct), or the hemoglobin (Hb), which are often used interchangably, depending upon the individual preference of the treating physician. They are used to determine anemia, to monitor conditions in which the blood loss occurs, chronic diseases, drug reactions, allergies, and the course of therapy.

The Hct of a sample of blood is defined as the ratio of the volume of erythrocytes (red blood cells) to that of the whole blood. It is expressed as a percentage or, preferably, as a decimal fraction. The units (L/L) are implied. The venous hematocrit agrees closely with the hematocrit obtained from a skin puncture; both are greater than the total body hematocrit.

Hemoglobin, the main component of the red blood cell, is a conjugated protein that serves as a vehicle for the transportation of oxygen and $CO_2$, throughout the body. When fully saturated, each gram of hemoglobin holds 1.34 ml of oxygen. The red cell mass of the adult contains approximately 600 g of hemoglobin, capable of carrying 800 ml of oxygen. The main function of hemoglobin is to transport oxygen from the lungs, where oxygen tension is high, to the tissues, where it is low. As used in this application the term hemoglobin (Hb) refers to the concentration of the iron-containing protein pigment found in red blood cells.

The Hct and Hb are often provided along with the total red blood cell count (RBC) which is usually expressed in the form of a concentration—cells per unit volume of blood. Once these three values are known (Hct, Hb and RBC), three red blood cell indices are calculated. These indices are particularly useful in the morphologic characterization of anemias. These values include the mean cell volume (MCV) which is the average volume of red blood cells and is calculated from the Hct and the RBC. Utilizing the formula:

$$MCV = Hct \times 1,000 / RBC \text{ (in millions per u)}$$

The mean cell hemoglobin (MCH) may also be calculated and is the content of Hb in the average red blood cell; it is calculated from the Hb concentration and the RBC utilizing the following formula:

$$MCH = \frac{Hb \text{ (in g per liter)}}{RBC \text{ (in millions per ul)}}$$

Another index calculable from the Hb and Hct is the mean cell hemoglobin concentration (MCHC). This index is the average concentration of Hb in a given volume of packed red blood cells. It is calculated using the following formula:

$$MCHC = \frac{Hb \text{ (in g/dl)}}{Hct}$$

Other characteristics of red blood cells which are available utilizing today's testing methods include values for the variability of the MCV about a mean value and estimates of abnormality in red blood cell morphology.

The above described indices are discussed in much greater detail in John Bernard Henry, M.D., *Clinical Diagnosis And Management By Laboratory Methods*, Part IV (17th edition 1984).

Modern clinical laboratory instrumentation has been built to make these primary analyses simultaneously in vitro on blood samples removed from the patient and the calculated indices are readily produced by these instruments. The calculated indices are often the preferred data on which physicians base their conclusions about a patient's condition.

A large number of testing methods, instrumentation, and techniques have been used in measuring and approximating values for Hct, Hb and RBC. The most common method used to determine the Hct (the ratio of packed red blood cells to volume of whole blood) involves centrifugation wherein a given blood sample is placed into a centrifuge for five minutes at approximately 10,000 to 12,000 g. The volume is then calculated by measuring the level of the red blood cells as a ratio of the total volume.

Sources of error in this method include insuring that the sample is subject to adequate centrifugal force for a sufficient duration so that the red cells may be packed and give an accurate reading. In addition, the final value must be corrected for trapped plasma present within the packed red blood cells. Technical errors in this method include failing to mix the blood adequately before sampling, improper reading of the level of cells to plasma, and irregularity of the inside diameter of the specimen tubes.

Methods used in the art to determine the Hb in a sample of blood include the cyanmethemoglobin method, the oxyhemoglobin method and the method of measuring iron content of the sample. Of the above three methods, the first (the cyanmethoglobin method) is recommended by the International Committee for Standardization in Hematology. That method involves diluting a sample of blood in a solution of potassium ferricyanide and potassium cyanide. The potassium ferricyanide oxidizes hemoglobins and potassium cyanide provides cyanide ions to form hemiglobincyanide which has a broad absorption maximum at a wavelength of approximately 540 nm. The absorbence of the overall solution can then be measured in a photometer or spectrophotometer at 540 nm and compared with that of a standard hemiglobincyanide solution.

The oxyhemoglobin method is not widely used, however it does yield reproducible results. The main disadvantage however is the lack of a stable standard with which to compare the results. This method involves the creation of a 1:251 dilution of blood in 0.007 N $NH_4OH$ utilizing distilled water. This solution is then shaken to insure proper mixing and oxygenation of the hemoglobin. The solution is read in a photometer with a green filter with a 0.007 N ammonium hydroxide solution used as a standard.

The last method listed above involves a procedure whereby Hb may be measured by determining the iron content of the whole blood. The non-hemoglobin iron in blood is negligible compared to hemoglobin iron, however, the iron must first be separated from the hemoglobin, usually by acid or by ashing. It is then either titrated with $TiCl_3$ or complexed with a reagent to develop color that can be measured photometrically since the iron content of hemoglobin is given as 0.347 percent, the concentration of hemoglobin in blood is calculated by dividing the iron concentration by 3.47.

Numerous sources of error are present in the above methods including those of the sample, the method, the equipment, and/or the operator. Errors inherent in the sample include improper venipuncture technique which may introduce hemo concentration, which will make hemoglobin concentration and cell counts too high. The photometer used for determining Hb must be calibrated in the laboratory before its initial use and must be rechecked frequently. The wavelength settings, filters and meter readings require constant monitoring.

The RBC, or red blood cell count may be determined by a number of different cell counting procedures. Any of these procedures includes three steps: dilution of the blood, sampling the diluted suspension into a measured volume, and counting the cells in that volume. Optical and electronic equipment have been developed to perform red blood cell counting, inter alia, in flowing systems in vitro. This equipment can also separately measure Hb by a chemical method in a separate analytic channel. The most widely used of such instruments is manufactured by Coulter Diagnostics of Hialeah, Florida, wherein red blood cells are passed through a glass tube with an aperture such that single cells can be detected based on a decrease in the voltage between electrodes positioned in a constricted portion of the tube. This measurement of voltage decrease yields an indirect value for RBC. The MCH is then computed utilizing the relationship:

MCH = Hb/RBC then the Hct is calculated from the relationship:

Hct = MCV × RBC after MCV is indirectly derived from the mean height of the voltage pulses formed during the red blood cell count.

Another instrument, made by Technicon Instrument Co., of Tarrytown, N.Y., and Fisher Scientific Co., of Pittsburgh, Pa., generates a value for RBC by using a system wherein red blood cells flowing in glass tubes are counted by deflection (scattering) of a beam of light that is directed to an opposing photo multiplier. Hb is measured by a chemical method in a separate channel of the instrument. The above-described instruments and methods are all characterized by their in-vitro analysis of specimen of blood withdrawn from the patient's body without the use of image analysis and yielding indirect (calculated or estimated) values for red blood cell indices.

Image analysis has been utilized to examine stained smears of blood fixed to glass slides with computer-controlled microscopes. Examples of such instruments include the "Hematrak" instruments manufactured by the Geometric Data Corp., Wayne, Pa. These instruments utilize pattern recognition software which identifies each of the major classes of white blood cells according to size, shape, staining and other morphologic characteristics. They also identify red blood cells for their morphology.

The imaging system includes a microscope with an automated scanning stage and an automatic focusing objective. Filters split the light transmitted through the stained cell into red, blue, and green portions of the spectrum. These allow the staining properties of the portions of the cells to be characterized. These instruments, however, do not produce any quantitative measures of red blood cells. These, and similar instruments, are also characterized by their in-vitro analysis of stained blood, fixed to slides for analysis. None perform quantitative analysis of red blood cell parameters.

Instruments which utilize flowing systems in conjunction with image analysis are exemplified by the International Remote Imaging Systems (IRIS) instruments which are designed to analyze in-vitro stream of the specimen flowing through glass tubing. This system utilizes a flow analyzer and system described in U.S. Pat. No. 4,338,024, issued to Bolz, et al., and assigned to IRIS. In that system, urine specimens are aspirated through a flow cell which is designed to orient cells and particles in one plane. Moving particles and cells are then photographed by a high-speed camera and counted by a microprocessor programmed to identify and classify the different particles and cells, including red blood cells. No quantitative analysis of red blood cell parameters is performed and the spectral analysis utilized is by transmission, rather than reflectance spectrophotometry.

A video computer system for measuring the lineal density of red blood cells and capillaries in vivo is described in an article by C. G. Ellis, et al. in *Microvascular Research* 27, Pages 1–13 (1984). This system utilizes a computerized frame-by-frame analysis of video images in order to perform continuous measurements of lineal density based on the spatial-average of blood opacity over a selected length of capillary. This method does not attempt to measure or even detect individual RBCs, but rather is directed to the measurement of light intensities along the centerline of the image of a capillary such that the number of RBCs in a given length of capillary is inversely related to he average light intensity over that length. A light intensity profile is determined utilizing a video analyzer which, for each frame, measured the light intensity values along a given length of capillary, first in the absence of RBCs to determine the "background light intensities" and then as the flow of RBCs is reestablished. A plot of mean opacity versus RBC for a particular capillary segment is then plotted and thus a value for RBC is estimated given a particular measured mean opacity. This system does not measure Hb, Hct or any of the other indices directly.

OBJECTS AND STATEMENT OF THE INVENTION

It is therefore an object of the present invention to provide an apparatus for in vivo analysis of red and white blood cell indices which eliminates the requirement that a specimen of blood be removed from the patient.

It is another object of the present invention to provide an apparatus for analysis of red and white blood cell indices which eliminates the pain and discomfort inflicted on the patient.

It is a further object of the present invention to eliminate the errors inherent in phlebotomy procedures.

It is another object of the present invention to provide an apparatus which eliminates the errors present in current in vitro analysis of red and white blood cell specimens by eliminating the need for chemical interactions, reagents, controlled materials, standards or calibrators.

It is another object of the present invention to provide an apparatus which is convenient to use and which provides immediate, accurate data on a patient without the need for a separate testing laboratory.

It is a further object of the present invention to provide a method of in vivo measurement of red and white blood cell indices quantitatively through the use of image analysis and reflectance spectrometry. These objects and others are accomplished by the present invention and particular embodiments of this invention are described herein below.

In one advantageous embodiment of an apparatus employing the present invention, a variant of a conventional ophthalmoscope is used to visualize and capture images of red and white blood cells in capillaries, small arteries or veins of the mucus membranes which line the inner surface of the eyelids and the exposed surface of the eye outside the iris (known as the conjunctiva), retina or other accessible sites on the mucus membranes. In these areas, capillaries are present whose visible appearance under magnification shows a continuous stream of blood. The opthalmoscope is used to identify and capture images of this blood flow in capillaries which are sized to allow the flow of only one or a few blood cells at a time to pass a given point. These images are captured from the lumen of the capillary, enlarged and fed into an appropriate computerized image analysis system. The images of numerous cells, potentially from many different capillaries, are capable of analysis by the system.

The computerized image analysis system directly measures characteristics of red blood cells including the boundaries of the individual red blood cell and, utilizing algorithms which relate area to volume, directly computes the volume of that particular cell. This measurement and calculation is carried out on a large number of red blood cell images captured by the ophthalmoscope which, when averaged, yield a direct measured value for mean cell volume (MCV) without the need for establishing or estimating the hematocrit (Hct) or red blood cell number (RBC).

The mean cell hemoglobin concentration (MCHC) is determined simultaneously with the direct measurement of MCV by measuring the intensity of red color (from the iron-containing protein pigment) which is attributable to that pigment. That intensity relates to a given concentration of hemoglobin within the cell. This measurement of intensity can be done either by incorporating a spectroscopic photodetector which selects and measures the wavelength peak maxima characteristics of hemoglobin or by incorporating a filter in an optical chopper that absorbs the wavelengths characteristic of hemoglobin to yield a value by subtraction spectral analysis. The volume of the captured red cell undergoing image analysis is known from given algorithms relating area to volume and the intensity is measured as indicated above. Together they yield a hemoglobin concentration for that particular red blood cell. As these measurements are carried out on a large number of red blood cells the mean cell hemoglobin concentration (MCHC) can be readily determined. From these two direct measurements, i.e. MCHC and MCV, the mean cell hemoglobin (MCH) can be readily calculated using the algorithm $$MCH = MCV \times MCHC$$

From the above indices, the Hb and RBC can be easily calculated.

While a relative value for the Hct can be measured, that measurement will not represent the central hematocrit as yielded by in vitro instrumentation in use in the art today. This difference stems from the fact that the present apparatus measures the Hct within the capillary itself as a proportion of the space within the still image occupied by red blood cells as opposed to the space which is not occupied by red blood cells. The central Hct, in contrast, represents the ratio of the volume of red blood cells to that of the whole blood as taken from a specimen removed from a vein of the patient and subject to centrifugation. These values can be easily correlated, however, through empirical analysis by comparing the direct measurement of the Hct from a specimen taken from the patient with the measured Hct derived from the indices measured above. This comparison will yield a conversion factor which can equate the two values. By this method the actual Hct can also be calculated from the measurements outlined above.

White blood cells (WBC) are approximately the same size or larger than RBC and are of sufficient size to be differentiated from the noncellular plasma. The white blood cell count can be readily determined using the same apparatus. The WBC in normal healthy individuals has a broad range of values with an average normal being 7,500 WBC per cubic millimeter. Given the fact that the RBC count also varies widely among normal healthy people with an average normal count being approximately 5,000,000 RBCs per cubic millimeter, an average normal healthy individual would have one WBC for every 667 RBCs in the circulation.

The apparatus of the present invention captures images of both white and red cells that pass through capillaries or venules. Those images are subjected to analyses their respective sizes, volumes and hemoglobin content. This last indice is done by subtraction reflectance spectroscopy. This also serves to distinguish between the WBCs and the RBCs since an unstained RBC is approximately $\frac{1}{3}$ hemoglobin and exhibits a distinctive red color. WBCs in contrast do not contain hemoglobin. Therefore they have no red color and show no difference in the reflected spectral properties. By keeping track of the ratio of WBCs with respect to the RBCs and accumulating a statistically reliable number, the actual ratio of WBCs to RBCs is determined. Furthermore, since the apparatus computes a RBC count, the WBC count is calculated using that ratio (RBC/WBC).

The results of computations for the directly measured parameters MCV, Hct and MCHC, and the calculated parameters MCH, Hb, WBC and RBC can then be printed on an appropriate report form which includes patient identification and demographics previously entered into the apparatus through separate input means, for example a keyboard. A visual display of histograms of these parameters can also be reviewed and printed as required. These results, including the numerical values and histogram displays, are retained in the computer memory and may be transmitted "on line" to a larger laboratory computer or maintained in memory as desired.

The foregoing and other objects, features and advantages of the present invention will become apparent from the description of preferred embodiments in connection with the accompanying drawings.

DETAILED DESCRIPTION OF PREFERRED EMBODIMENTS

Figure 1:
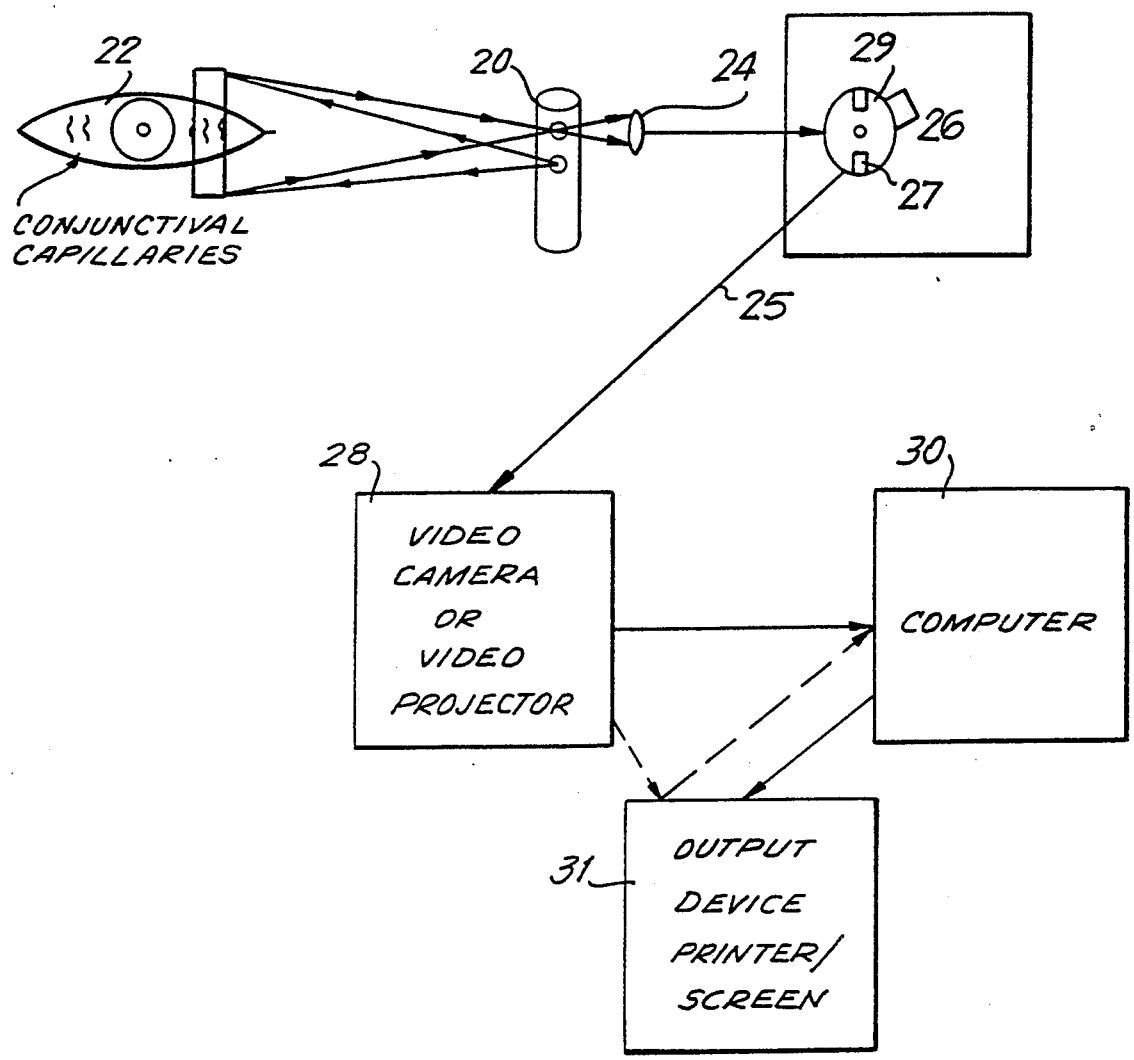
FIG. 1 is a schematic block diagram of an apparatus in accordance with one embodiment of the present invention.
Figure 2:
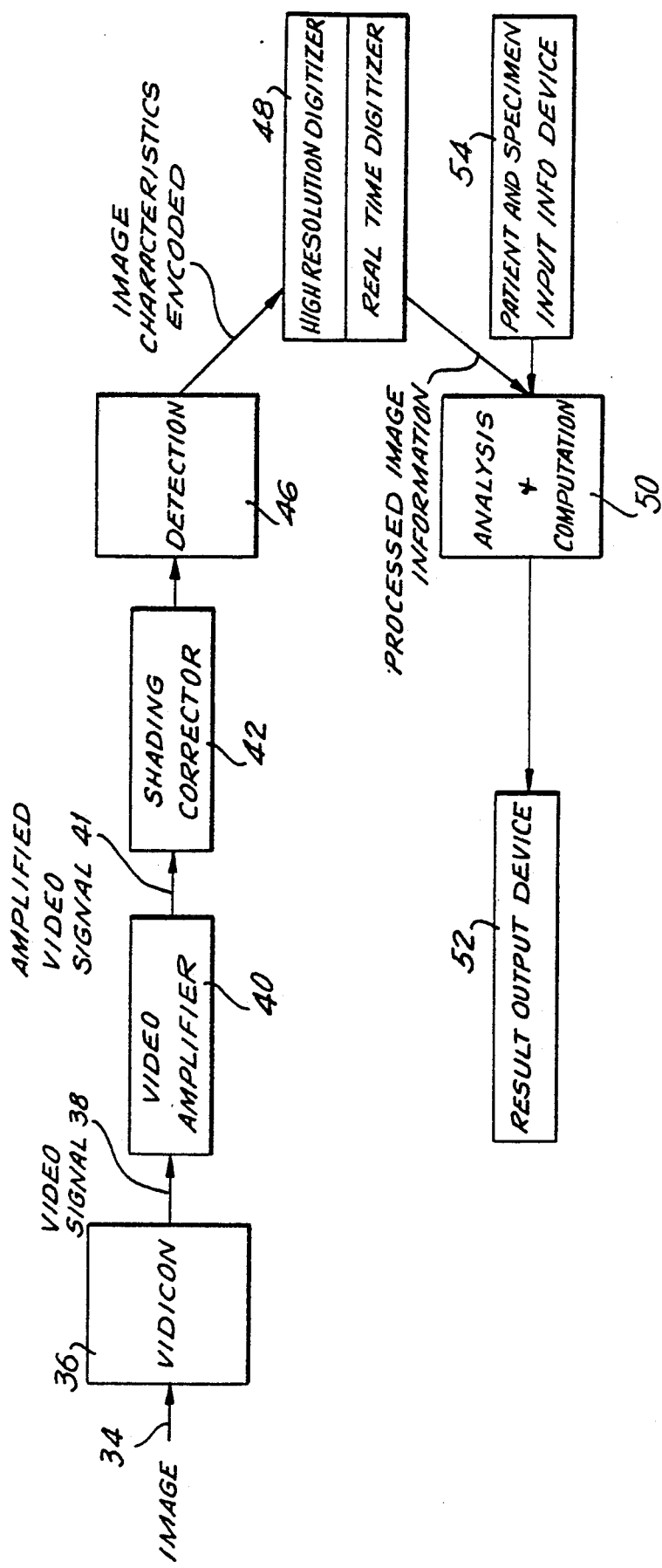
FIG. 2 is a schematic block diagram of video analysis components of one embodiment of the present invention.

Referring now to the drawings and, in particular, to FIGS. 1–2, there is depicted one embodiment of an apparatus in accordance with the present invention. FIG. 1 shows a schematic block diagram of one preferred embodiment including a focusable light source and visual image receiver 20 for capturing images of the red blood cells in conjunctival capillaries of the eye 22. This focusable light source and visual image receiver (FLS-VIR) is preferably a conventional ophthalmoscope or slit lamp similar to those manufactured by Welch-Allyn of Skaneateles Falls, N.Y., or Zeiss Co. Either of these conventional FLS-VIR devices can be equipped with additional magnification capability to make them adaptable for use with the present invention. Since red blood cells average 7.4 microns in diameter and have an average volume of 87 ±5 cubic microns, some magnification is necessary for accurate analysis. This magnification falls within the range of from 150X to about 650X depending upon the analysis equipment used.

Conventional ophthalmoscopes provide approximately ten-fold magnification of the focused image. This is sufficient for selection of the field for testing and for focusing of the image however increased magnification is necessary for subsequent image analysis and reflectance spectroscopy.

Slit lamps provide approximately a forty-fold magnification to the viewer. This magnification is sufficient for visualizing individual red and white blood cells flowing within the capillaries however subsequent image analysis and spectrophotometry would require further magnification. Both ophthalmoscopes and slit lamps have substantially more components and capabilities than are required for the present invention. For this reason, the instrument necessary for image analysis and reflectance spectroscopy can be added to pre-existing components or integrated with a simplified version of an ophthalmoscope which includes only the light source, focusing capability and the image receiver.

Sufficient light must be available to permit ordinary visualization of the small blood vessels of the conjunctiva, including the capillaries, arterioles and venules. The conjunctiva will be referred to herein in further descriptions however it is important to note that other sites can also provide satisfactory images of red cells in vivo according to the present invention. The conjunctival capillaries are preferred because they are readily accessible and provide an excellent contrast between the red blood cells in the capillaries and the white background of the conjunctiva.

The FLS-VIR 20 is adapted to allow for subsequent image splitting, and transmission to an optical enlarger 24 for enlargement and processing. Transmission of these images is preferably through fiber optic transmission lines, however, any appropriate transmission medium is acceptable.

Subsequent processing and transmission of the images captured and magnified by the FLS-VIR can include for example slit lamp cameras and/or video camera attachments similar to those used for operating room ophthalmoscopes, micro-surgical devices and television ophthalmoscopy.

In one particularly advantageous embodiment of the present invention, the elements of the FLS-VIR can be mounted in a rigid assembly wherein the patient's head is maintained in a fixed cradle similar to current slit lamp fixtures. Utilizing this arrangement, the image can be viewed directly by the physician and also split to a side viewing port for subsequent computerized image analysis.

The image splitter discussed above diverts a portion of the image visualized by the operator and subjects that image to further analysis. The image splitting can be accomplished by several well-known techniques utilizing various optical devices. These devices include partially reflective mirrors and interspersed fiber optical strands.

Instrumentation for this subsequent analysis includes an image magnifier 24, a light chopper and filter 26 and a video camera scanner or projector 28. The images produced directly on the pickup tube of an ordinary vidicon-type television camera would be approximately 9.4 × 12.5 mm and require approximately 1.0 foot candles. This image can be displayed on a printer/screen 31 either prior or subsequent to analysis by computer 30.

Alternatively, the split image of the blood cells can be passed through the beam splitter enlarging optics 26 and filtered either before or after being transmitted by fiber optics transmission lines to a television pick-up tube. Video signals of sufficient quality for image analysis are produced by silicon diode vidicons that have a 5-10X sensitivity of standard vidicons, with light levels of 0.1 to 0.2 foot candles at the base plate of the tube. A phosphor screen-fiber optic device may be employed, such as is used to obtain images from transmission electron-microscopy (TEM), with a sensitive TV screen also equipped with fiber optics. Weak signals may be enhanced through electronic amplification and/or computer processing of the signals that reach the vidicon so that accurate image analysis can be performed.

In each case, the captured image is presented to a video camera which subsequently transforms the image into electronic information to be subsequently analyzed by computer 30.

Hb analysis is performed by interposing an optical chopper shown generally at 26 in line with the image transmission. The chopper consists of a conventional motor driven wheel 29 having a filter slot with an appropriate filter 27. That filter 27 is designed to absorb the specific energy in the red portion of the spectrum corresponding to the maxima of absorption of the hemoglobin of red blood cells. This maxima is generally in the range of about 650 nm. The filter should have a broad absorption band width on either side of the maxima in order to remove the light characteristic of hemoglobin from the subsequent image and image processing. This light characteristic results during the very short instant when the rotating wheel interposes the filter between the primary image of the red cell that has been illuminated with white light and a subsequent image or transformed data representing the earlier image. The instantaneous image of each red blood cell analyzed by the instrument will be presented both with and without the intensity of red light that is entirely attributable to the iron-containing protein pigment of hemoglobin. The hemoglobin concentration of each red blood cell will then be determined by subtraction of the signal generated by the pigment from the background in the same cell and calculated according to Beers' Law as modified by the characteristics that change in the case of reflectance vs transmission spectroscopy and may be confirmed empirically. Utilizing this technique, a computer receiving this data performs subtraction reflectance spectrometry to determine the hemoglobin concentration of each individual red blood cell analyzed.

The Optical Image Receiver Enhancer-Enlarger (OIREE) functions to receive, encode, and, in one version, to enlarge the image and make it suitable for visual analysis and display by other components of the instrument. The receiving component of the OIREE is, in one embodiment, a high speed video camera with a very rapid shutter sufficient to allow the capture of instantaneous images of red blood cells. The shutter speed should be slow enough to allow the optical chopper described above to provide an image with and without red filtering, and yet fast enough to preserve discrete cell margins without blurring. Ordinary vidicons, silicon diode vidicons with high sensitivity or such vidicons as the "15-3 precision scanner" used by Bausch &

Lomb in the Omnicon 5000, can be employed. These vidicons may be combined advantageously with software to accommodate and correct for non-uniform distributions of light falling on the vidicon so as to make the signals readily analyzable by the image analysis components of the apparatus.

Optical enhancement can be achieved by several established techniques. The primary function of this component is enlargement. The unenhanced image can be enlarged through conventional optics by means of a series of lenses as in a telescope or microscope. Alternatively, the image that has been received directly into a video camera can be enlarged by the action of the video camera. This enlarged image is then operated upon by image enhancement programs to detect, clarify and sharpen boundaries between red blood cells and their surroundings, and to enhance color characteristics. This component may, alternatively, be positioned in line before, after, or among several others of the instruments depending upon the preferred configuration.

The enlarged image from the OIREE is preferably projected on to a video screen. The raster of this screen can provide subsequent enlargement and enhancement functions where the OIREE has not yet operated upon the enlarged image of the red blood cell and is essentially functioning only as a video camera projection.

Alternatively, the video camera can record the continuously generated captured images on to a recording medium such as video tape, which can then be played into the video projector at varying speeds and used to obtain images for subsequent analysis by Computer 30.

As detailed in FIG. 2, a series of light images 34 of flowing red and white blood cells are produced on the photo sensitive face of a special vidicon camera tube 36 by an optical system which includes an image splitter, a light chopper-filter, enlarging optics and a signal amplifier. The brightness forming the image at each point on the screen is converted into electrical voltages by repeatedly scanning the image with an exploring spot formed by the electron beam of the camera tube. This spot generates an electrical video signal which indicates the brightness at each of its instantaneous positions. The video signal 38 is amplified in a conventional video amplifier 40 and may, optionally, be combined with a video display (not shown). That signal determines the brightness of a reproducing spot formed by the display tubes' electron beam. The reproducing spot moves over the latter screen synchronously and is coordinated with the exploring spot. The reproducing spot reconstructs the brightness distribution of the image that was received on the vidicon camera face with the possibility of enlargement and/or amplification of signal intensity. The amplified video signal 41 is then subject to correction for "shading" and sensitivity adjustment. The corrected amplified video signal 44 is then encoded 46 for subsequent translation into critical information.

Conversion of the signal to digital values is accomplished by a high resolution digitizer 48 and occurs in real time. These values are transmitted to a computer through a data base and memory register. The video signal that actually produces the video display is generated from this memory. The system may also be provided with a separate input means 54 such as a keyboard so that patient and specimen information can be included in the display and analysis.

Alternatively, charge coupled devices can be substituted for the conventional optics described above. Since charge coupled devices have very short focal lengths, as little as 3 mm they permit the accumulation of images near to the point being visualized. Those images are then transmitted in digitalized form through electrical wires to an image receiver such as a decoder (not shown) and vidicon 36. Substitution of the charge coupled device obviates the need for a fiber optic cable and thus is less fragile and less expensive.

In one such embodiment, a charge coupled device is fixed in the back of a cushion-edged cup-like shell. This shell can be disposable. The shell is designed to fit against the frontal and maxillary protuberances over and around the eye in order to insure proper alignment of the charge coupled device. Enlargement of the image is achieved by interposing a lens in the shell housing, between the conjunctive and the charge coupled device.

Lighting for the observable field of the charge coupled device is provided by a fiber optic light source. One such light source is a rapid strobe pulse capable of being pulsed at such a speed that they appear to be a continuous light source to the ordinary human eye, approximately 80 times per second. Such a strobed light source produces discontinuous still images that can be more readily received and processed by the video camera 28 than continuous images. A further advantage is derived wherein the strobed light is flashed at different wavelenghts using devices such as rotating filters. This effectively controls the wavelength output of light that strikes the observed field. Thus, a light of preferred wavelength for hemoglobin quantification (approximately 540 nanometers) illuminates the same image received 1/80th of a second earlier. This technique permits background subtraction between the two consecutive images.

Computer 30 performs analyses the data representing the images of red blood cells developed by the previously described components. From this data, the red and white blood cell analyses and indices are produced. The functions carried out by the computer include image analysis to determine the size of each red blood cell analyzed. Image processing programs will select only those red blood cells which conform to preselected criteria. That criteria insures uniform orientation of the cells so that they are imaged with their maximal surface perpendicular to the optical path. Since red blood cells circulate as biconcave discs, the boundaries and surface features of the flat planar oriented biconcave discs allows for ready discrimination of the orientation required for utilizing a particular cell for image analysis. A simple criterion incorporated in the image processing algorithm identifies red blood cells as acceptable for further analysis. Such criterion, for example, could require that the maximum diameters in the X and Y axes differ by no more than ±2%. Consistent deviation from this criteria would indicate important morphological abnormalities such as poikilocytosis or sickle cell anemia, and would generate a report notation that further examination of this patient is appropriate.

WBC count is determined by compiling the ratio of WBCs with respect to RBCs in the captured images and accumulating a sufficient number of images to achieve statistical reliability. By multiplying the computed RBC count by the ratio of WBC/RBC a WBC count for the patient can be calculated.

For example, if the determined ratio of WBCs to RBCs is one in a thousand and the RBC count is known to be five million, the WBC count would be five thousand. Where the ratio is one WBC to two hundred fifty RBCs and the RBC count is five million, the WBC count would be 20,000.

Analytical programs for image analysis, computation and presentation of results can be permanently stored in the memory of the computer. Given the very great number of cells flowing past the visualized field in any instant, there will be sufficient numbers conforming to the strict orientation criteria discussed above such that analysis of cells having the same uniform special orientation can be selected for quantitative analysis. This analysis will produce a direct measured value for the cell volume of each imaged cell. When this number is averaged over numerous cells, the MCV is acquired through direct measurement. This MCV value, determined in vivo will be more accurate than that approximately calculated utilizing in vitro analysis of blood samples obtained through phlebotomy. For purpose of comparison these values for MCV can be made equivalent by obtaining samples of blood simultaneously with measurements made by the new apparatus. Comparison of a great number of these values will establish an empirical correlation from which calculation algorithms can then be incorporated into computer to assure that the values yielded by the instrument will correspond to those values currently generated by in vitro instrumentation. This will serve to avoid confusion and provide the physician with values in a familiar range.

Additional image analysis performed by computer yields a ratio of red blood cell area to non-red blood cell area in numerous imaged fields. Given a sufficient sampling of instantaneous image fields captured as described above, a calculation of this ratio of red blood cell area to non-red blood cell area will approximate the true hematocrit (Hct), which is the volume of red blood cells as a percentage of the volume of whole blood. This value may also, optionally, be correlated with values of Hct provided by current in vitro instrumentation.

Direct determination of hemoglobin concentration (Hb) of each individual cell is accomplished in one embodiment by means of subtraction reflectance spectroscopy. This involves measuring and recording the signal intensity attributable to the hemoglobin present in each image of a given red blood cell and then subtracting the signal intensity by means of a light chopper-filter described previously. This will produce a direct value for cell hemoglobin concentration, which, when averaged over numerous cell images, will approximate the recognized value for mean cell hemoglobin concentration (MCHC). Empirical correlations of this value with values determined through in vitro instrumentation can be determined by establishing the deviations through simultaneous measurements and incorporating those deviations into the computer component of the apparatus to assure equivalence.

The computer will accumulate the results of the numerous analyses discussed above and will perform statistical analysis to compute the mean, and coefficients of variation for each measured parameter. This primary data is stored for various visual displays, such as for example histograms or other pictorial representations of the cell analysis or the cells themselves.

From the above data the computer will calculate conventional red blood cell indices and analyses as shown below.

MCV - directly measured
MCHC - directly measured

MCH - obtained by calculation: $\frac{MCHC}{MCV} = MCH$

Hct - directly measured
Hb - obtained by calculation: RBC = Hct/MCV
(confirmed by calculation: Hb = MCH × RBC)
RBC - obtained by calculation: RBC = Hct/MCV
(confirmed by calculation: RBC = Hb/MCH)
WBC - obtained by calculation: WBC = RBC × (RBC/WBC)

The computer will store the above measured and calculated indices for printout, display or uploading to a larger computer, for example a laboratory or hospital computer or may store the data for later statistical analysis. The apparatus may optionally include conventional peripheral devices for input of patient identification and other demographic information similar to that currently utilized prior to an laboratory testing.

The Output Device 52 can be any appropriate instrumentation such as CRTs, VDTs or printing devices wherein the results of the red blood cell analysis can be provided either on screen or hard copy. It is preferably capable of holding data for immediate viewing, printing or transmission.

The foregoing is considered as illustrative only of the principles of the present invention and is not limited to the particular embodiments discussed herein. Various changes, substitutions and modifications may be made thereto by those skilled in the art without departing from the spirit or scope of the invention defined by the appended claims.

What is claimed is:

1. Apparatus for in vivo determination of red and white blood cell characteristics from a flow of blood cells in mucus membranes comprising:
   image capturing means for optically isolating individual blood cells in at least one flow of blood cells in said mucus membranes;
   image receiving means for receiving a plurality of still images of said blood cells from said image capturing means;
   filtering means for interposing light filters on said images; and
   means for determining blood cell characteristics MCV, Hb, MCHC, RBC and WBC from said still images.

2. Apparatus as in claim 1 further comprising display means for displaying said blood cell characteristics.

3. Apparatus as in claim 2 further comprising image enlarger means disposed between said image capturing means and said image receiving means for enlarging said still images.

4. Apparatus for in vivo determination of red and white blood cell characteristics from a plurality of still images of blood cells flowing in capillaries of mucus membranes comprising:
   image capturing means for optically isolating images of red and white blood cells in at least one capillary wherein only a few blood cells may pass a given point simultaneously;
   filtering means for alternatively interposing optical filters on red and white blood cell images isolated by said image capturing means;
   image receiving means for receiving said plurality of filtered images and including means for translating said filtered images into electronic data;

analysis means connected to said image receiving means for determining individual red and white blood cell characteristics MCV, Hb, MCHC, MCH, RBC and WBC from said electronic data; and display means for displaying said blood cell characteristics.

5. Apparatus as in claim 4 further comprising fiber optic transmission means for conducting said captured red and white blood cell images to said image receiving means.

6. Apparatus as in claim 4 wherein said image receiving means comprises:
a vidicon tube means for receiving images from said image capturing means and transmitting said images in the form of a video signal;
a video amplifier means for amplifying said video signal;
a shading corrector means for correcting said amplified video signal;
a detection device means for encoding image characteristics from said corrected amplified video signal; and
a digitizer means for processing said encoded image characteristics.

7. Apparatus as in claim 6 which further comprises:
a computer means interfacing with said digitizer to receive and analyze processed image information; and
input means for entering data into said computer.

8. Apparatus as in claim 4 wherein said image capturing means is a slit lamp device.

9. Apparatus as in claim 4 wherein said image capturing means is a charge coupled device.

10. Apparatus as in claim 9 further comprising a strobed fiber optic light source means to illuminate a desired flow of blood cells.

11. Apparatus as in claim 4 wherein said image capturing means is an ophthalmoscope.

12. Apparatus as in claim 4 wherein said filter means is an optical chopper comprising:
a rotatable wheel having a slot therein in line with image transmission; and
a filter held in said slot, said filter adapted to have a maxima of absorption corresponding to the maximum reflected by hemoglobin.

13. Apparatus for in vivo determination of red and white blood cell characteristics from a flow of blood cells in mucus membranes comprising:
an ophthalmoscope means having a magnification range of from 150X to about 650X for capturing images of blood cells from said flow of blood cells;
an image splitter means connected to said ophthalmoscope means for diverting a portion of the captured images;
an image magnifier means connected to said splitter for magnifying said diverted captured images;
a light chopper and filter means connected to said image magnifier means for alternately interposing a filter on said diverted captured images;
a video camera scanner means connected to said light chopper and filter means for receiving and translating said diverted, captured, filtered and unfiltered images of blood cells into electronic information;
a computer means connected to said video camera scanner means for receiving said electronic information and determining blood cell characteristics of MCV, Hb, MCHC, MCH, RBC and WBC therefrom using analytical programs for image analysis and computation.

14. Apparatus as in claim 13 further comprising an output device means for displaying said blood cell characteristics.

15. Apparatus as in claim 13 wherein said ophthalmoscope, image splitter, image magnifier, light chopper and filter, video camera scanner and computer means are connected by means of fiber optic transmission lines.

16. Apparatus for in vivo determination of red and white blood cell characteristics including MCV, MCHC and Hct from a flow of blood cells in mucus membranes wherefrom MCH, Hb, RBC and WBC can be calculated, said apparatus comprising:
a focusable light source and visual image receiver means for identifying and capturing individual red and white blood cell images in at least one capillary wherein only a few blood cells may pass a given point simultaneously;
a light chopper and filter means connected to said focusable light source and visual image receiver means for alternatively interposing a filter on said captured images;
an optical image receiver enhancer-enlarger means connected to said light chopper and filter means for receiving, encoding and enlarging said images to make them suitable for visual analysis;
a video screen means connected to said optical image receiver enhancer-enlarger means for receiving and projecting said enlarged images; and
a digitizer means connected to receive said enhanced and enlarged images and to convert said images to digital values;
a computer means connected to said digitizer means for receiving said digital values and computing blood cell characteristic including MCH, Hb, RBC and WBC from measured characteristics MCV, MCHC, Hct.

17. Apparatus as in claim 16 further including an output device connected to said computer for displaying said blood cell characteristics.

18. A method for in vivo determination of red and white blood cell characteristics from a flow of red and white blood cells in mucus membranes comprising:
capturing a plurality of optical images of a flow of red and white blood cells in said mucus membranes;
filtering said images by alternately interposing optical filters thereon;
translating said images into electronic data for analysis; and
electronically analyzing said electronic data to determine characteristics MCV, Hb, MCHC, MCH, RBC and WBC of blood cells.

19. A method as in claim 18 which includes the step of displaying said characteristics.

20. A method as in claim 18 wherein the red blood cell characteristics of mean cell hemoglobin concentration and mean cell volume are determined by image analysis.

21. A method as in claim 18 wherein said analyzing of electronic data includes subtraction reflectance spectrometry to determine hemoglobin concentration of red blood cells in vivo.

22. A method as in claim 18 wherein said flow of red and white blood cells is isolated in the conjuctiva area of the eye.

* * * * *